US006685662B1

(12) United States Patent
Curry et al.

(10) Patent No.: US 6,685,662 B1
(45) Date of Patent: Feb. 3, 2004

(54) WEIGHT BEARING SHOULDER DEVICE

(75) Inventors: Mark E. Curry, Stuart, VA (US); Charles Price, Mount Airy, NC (US)

(73) Assignee: Therapeutic Enhancements, INC, Martinsville, VA (US)

( * ) Notice: Subject to any disclaimer, the term of this patent is extended or adjusted under 35 U.S.C. 154(b) by 0 days.

(21) Appl. No.: 10/152,741

(22) Filed: May 23, 2002

Related U.S. Application Data

(60) Provisional application No. 60/305,189, filed on Jul. 16, 2001.

(51) Int. Cl.[7] .................................................. A61F 5/00

(52) U.S. Cl. ........................................................ 602/20

(58) Field of Search ................................ 602/4, 20, 21, 602/60–62, 5, 16; 128/19, 874; 482/124; 601/33, 24, 26, 89

(56) References Cited

U.S. PATENT DOCUMENTS

| | | | | | |
|---|---|---|---|---|---|
| 3,698,389 | A | * | 10/1972 | Gudel | |
| 3,754,547 | A | | 8/1973 | Walker | 128/25 R |
| 5,020,521 | A | * | 6/1991 | Salort | |
| 5,052,681 | A | | 10/1991 | Williams | |
| 5,207,626 | A | | 5/1993 | Einhorn | 482/123 |
| 5,308,305 | A | * | 5/1994 | Rommney | |
| 5,417,643 | A | * | 5/1995 | Taylor | |
| 5,913,749 | A | | 6/1999 | Harmon | 482/49 |
| 5,993,362 | A | * | 11/1999 | Ghobadi | |
| 6,113,562 | A | * | 9/2000 | Bonutti | 482/124 |
| 6,165,111 | A | | 12/2000 | Walker | 482/904 |

* cited by examiner

*Primary Examiner*—Jerome W. Donnelly
(74) *Attorney, Agent, or Firm*—Patent & Trademark Services Inc; Thomas Zack; Joseph H. McGlynn

(57) ABSTRACT

A rehabilitation device having a shoulder brace with depending adjustable tensioning straps mounted to the shoulder brace on one end and to a hand mount on the other end.

6 Claims, 2 Drawing Sheets

WEIGHT BEARING SHOULDER DEVICE

Applicants claim the benefit of the U.S. Provisional application No. 60/305,189 filed on Jul. 16, 2001.

BACKGROUND OF THE INVENTION

The present invention relates to a rehabilitation device that applies a force to the extremities of a user.

The benefits of constraint induced therapy for stroke afflicted limbs have been discussed in several articles. Results suggest the benefits can be obtained using constraint induced movement therapy. Persons with damage to their extremities may receive considerable benefit by having weight bearing forces placed on the extremities. One way to apply forces such forces is to simulate weight bearing activities applied to the extremities. Resistive forces like springs may be used to simulate weight. As the user moves a handle or other mechanism against the normal biasing force applied by the spring, a resistive force is encountered allowing the patient to receive beneficial results. It is desirable that the amount of force applied to the extremity be adjustable and that the mechanism for applying the force be carried by the user to insure its ready availability and convenient use.

DESCRIPTION OF THE PRIOR ART

Constraints that apply forces to the extremities of a user are known to the prior art. For example, U.S. Pat. No. 3,754,547 to Walker discloses a therapeutic exercise device with positioning for the hands and feet of the user and yield able resistance means to be overcome.

U.S. Pat. No. 5,052,681 to Williams discloses hand held rehabilitation and exercise device with tubular resistance.

U.S. Pat. No. 5,207,626 to Einhorn discloses a device for exercising the scapula related muscles. A harness fits over the shoulder an and upper arm with straps and springs.

U.S. Pat. No. 5,913,749 to Harmon discloses a resistance exercise apparatus that receives a body extremity. Resistance means are provided to impose resistance against the movement of the body extremity.

U.S. Pat. No. 6,165,111 to Walker discloses a therapeutic exercise apparatus with a tubular post pivotally mounted to a base with springs to keep the post upright.

In the present invention is a shoulder brace having two depending members with each member having tension adjustable straps mounted to the shoulder brace on one end and to a hand mount on the other end, all as will be detailed in the specification that follows hereafter.

SUMMARY OF THE INVENTION

This invention relates to a rehabilitation device having a shoulder brace with depending aligned members with the members having tensioning adjustable straps mounted to the brace on one end and to a hand mount on the other end.

It is the primary object of the present invention to provide for an improved rehabilitation device that can apply a tensioning force to extremities.

Another object is to provide for such a device that includes a shoulder brace, tensioned arm straps and a connected hand mounted yoke.

These and other objects and advantages of the present invention will become apparent to readers from a consideration of the ensuing description and the accompanying drawings.

DESCRIPTION OF THE PREFERRED EMBODIMENT

Figure 1:
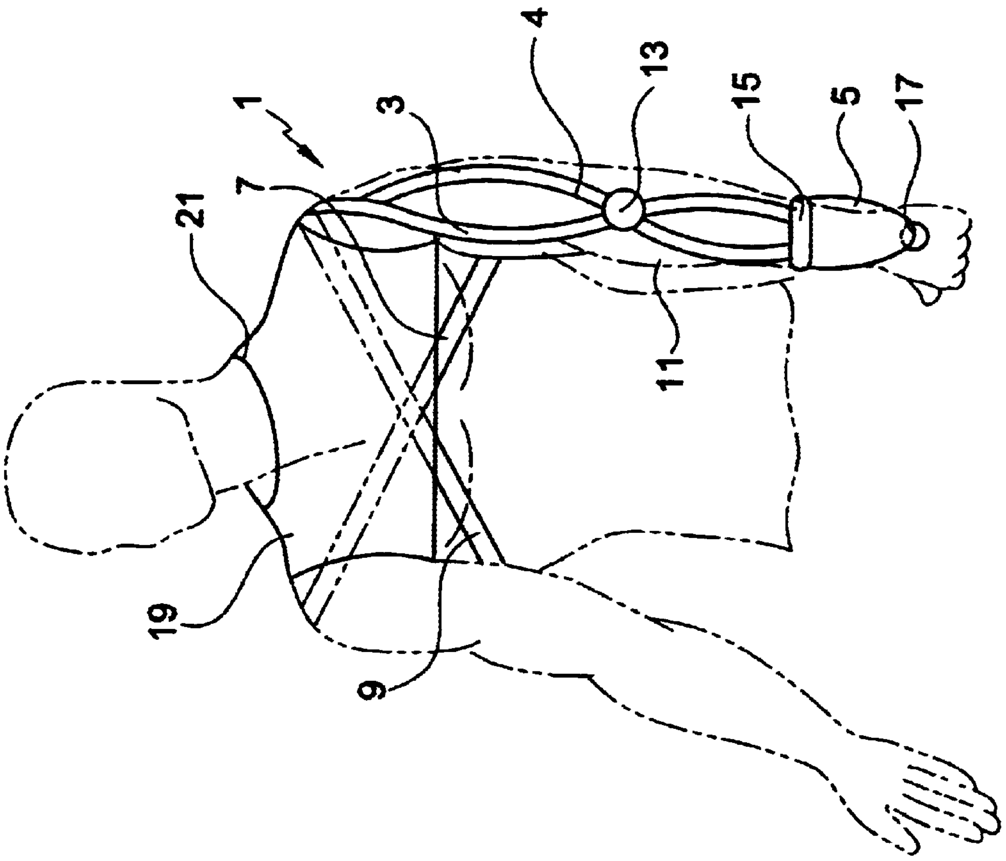
FIG. 1 is a front view of the present invention.
Figure 3:
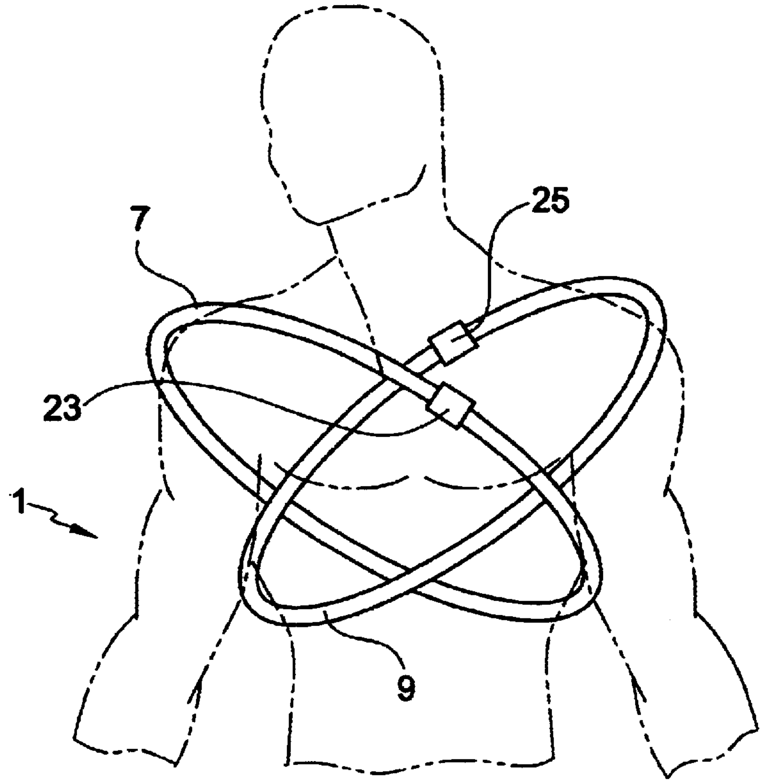
FIG. 3 is a perspective view of the shoulder brace.

FIG. 1 is a front view of the present invention. The present invention has a shoulder brace 1, arm straps 3, 4 that depend from brace 1 and a hand yoke 5. The shoulder brace 3 consists of two straps 7 and 9 that go around a user. Straps 7, 9 are arranged in a criss cross manner and intersect at the front and back of a user, as best shown in FIG. 3. Each strap 7, 9 has a front accessible length adjustment mechanism. A flexible webbing material may be used for each shoulder strap 7, 9 to insure the strap will conform to the lateral aspects of the user's shoulders.

Fixed to the each of the shoulder straps 7, 9 is one of the two depending arm straps 3, 4, respectively. The arm straps 3, 4 are spaced apart from each other above the elbow along the length of the user's arm 11, shown in dotted line format. Arm strap 3, 4 can be made of a material that can subjected to a tensioning force without easily breaking, such as an elastic or rubber material. Near the elbow of the user is a conventional tension adjustment mechanism 13 for each strap 3, 4. By shortening the length of each strap, the mechanism 13 may place one or both of the straps under greater tension. Below mechanism 13 the straps 3, 4 are again spaced apart until they join the hand yoke 5.

Hand yoke 5 is generally funnel shaped and may be made of aluminum. Yoke 5 may be padded along the interior portions which bear against an Inserted arm/wrist and hand of a user. The yoke 5 may be a closed funnel, as shown, or may be an open frame structure. The illustrated V-shaped yoke 6 extends over the wrist of a user. At the lower or apex of the V-shaped yoke there is a hand grip 17. A top opening 15 allows the user to insert their hand from above into the yoke 5. There In the yoke 5 is a smaller lower opening. Fixed across this lower yoke 5 opening hand grip 17. Grip 17 allows a user to wrap their fingers around the grip to form a firm connection with yoke 5 and the attached arm straps 3, 4 and shoulder straps 7, 9.

Covering most of the shoulder straps 7, 9 is small vest 19. Vest 19 may cover all or part of the upper torso of the user. A head opening 21 surrounds the neck of the user. Shoulder straps 7, 9 may be fixed to vest 19. To provide for a firmer anchor along with the shoulder straps fixed to the arm straps 3, 4, a portion of the vest 19 adjacent the straps may also be fixed to the straps.

Figure 2:
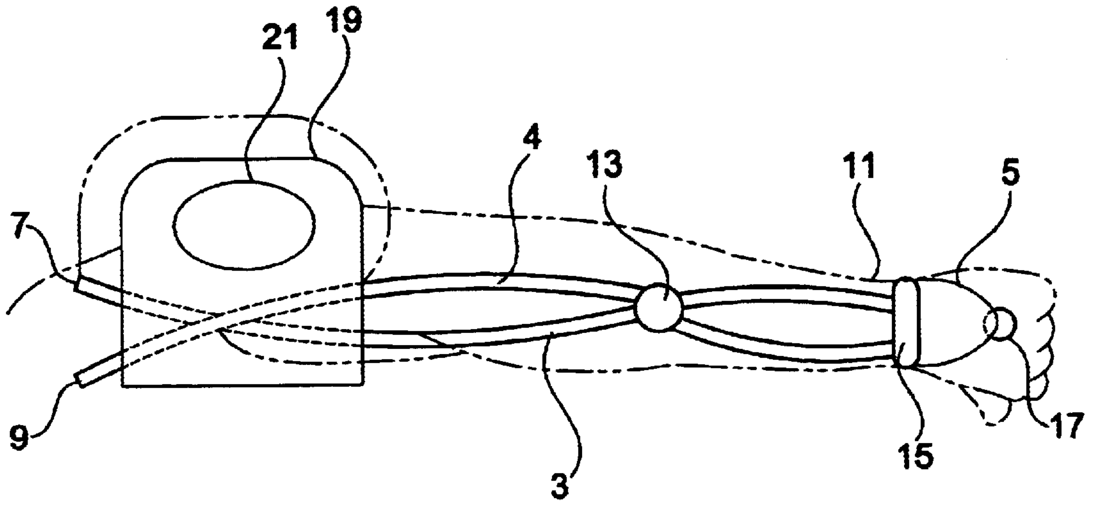
FIG. 2 is a top view of the invention.

FIG. 2 is a top view of the invention. In this view the arm 11 of the user is raised about 45 degrees from vertical in relation to that shown in FIG. 1. The user's head, previously shown in dotted line format, has been omitted. Vest 19 extends over most of the shoulder straps 7, 9 on the engaged front and back portions of the user's upper torso. Shoulder strap 7, 9 intersect each other twice, one on the front (shown) and again of the back (not shown) of the user. Yoke opening 15 of allows access to the interior of the funnel shaped yoke. Handle grip 17 extends across a bottom opening of yoke 5 and is fixed to the yoke. By wrapping the hand and fingers around grip 17, the extremity is subjected to the tensioning force applied to it by the connected taut straps 3, 4. If more applied tension is desired, the straps' length adjustment mechanisms 13 may be used.

FIG. 3 is a perspective view of the shoulder brace 1. Each shoulder strap 7,9 can form a closed loop. Each strap loop goes over one shoulder of the user and under an opposite side arm pit. At the front side of each shoulder strap 7,9 is a conventional length adjustment mechanism 23, 25, respectively. By changing the lengths of each shoulder strap 7,9, the formed loop has its circumference varied. For a slim person the formed strap loops can be given a smaller circumference and for a larger person a larger circumference. An arm strap is fixed to each shoulder strap with one arm strap 3,4 being on an opposite side of the user's arm, as shown in FIG. 1

Additional modifications may be made to the disclosed embodiment. One such modification would be to change the arm straps to cables and to cover the cables with a flexible tubing material along their lengths. Another possible modification is to use a covering for the arm straps such as that used to mead a broken arm. The same covering could have side VELCRO straps to allow access to the arm strap and their adjust length mechanism to adjust tension applied to the hand.

By forming a firm anchor on one end attached to the user's body, with an adjustable strap type of attachment fixed to an extremity mount, a tensioning force may be applied to the yoke mounted extremity. Variations in the amount of tension applied can be made. Additionally, one or both of the arms can be mounted with straps fixed to the same shoulder brace with each hand having its own hand grip or extremity mount.

Using the principles described, the shoulder brace 1 can hold the wrist in an extended position and the elbow in an extended position to provide tension across the wrist, elbow, and shoulder joint using the hand and vest as anchoring points. The tension of the brace is used to produce approximation or compression of the shoulder elbow, and wrist joint, simulating weight bearing. This action increases stimulus to proprioceptors of muscles and joints of the upper extremities to promote movement.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What we claim as our invention is:

1. A rehabilitation device comprising:

a shoulder brace having depending aligned members, said depending aligned members having tension adjustors, said tension adjustors comprising two separate straps, each of said two separate straps having a length and being made of a flexible material, each of said two separate straps having means to shorten the length of the separate straps to place the strap under tension, a hand mount connected to said depending aligned members at an end opposite said shoulder brace, and said hand mount comprising a yoke which is generally funnel shaped to receive and bear against the inserted wrist of a user.

2. The rehabilitation device as claimed in claim 1, wherein said hand mount is padded along the interior portion of the yoke, said yoke having a top opening and a smaller lower opening with said hand mount extending across the smaller lower opening.

3. The rehabilitation device as claimed in claim 2, wherein said shoulder brace comprises intersecting trap loops with each loop extending around the upper torso of a user.

4. The rehabilitation device as claimed in claim 3, wherein each of the shoulder brace strap loops have a length with an adjustment mechanism.

5. The rehabilitation device as claimed in claim 4, also including a vest that extends over the upper torso of a user, said vest covering most of the shoulder brace strap loops with the straps being fixed to the vest, and said vest having an opening to receive the inserted head of a user when the vest is mounted on the upper torso of the user.

6. A rehabilitation device comprising:

a shoulder brace having connected depending members which extend from the shoulder brace, said depending aligned members having tension adjustors, said depending aligned members comprising two separate straps that have a length with each of said two separate straps intersecting each other along their respective lengths, each of said separate straps being made of a flexible material, each of said separate straps having their tension adjustor means located where the straps intersect each other to provide for the shorting of the length of the each of the separate straps, a hand mount connected to said depending aligned members at an end opposite from where connected to the shoulder brace, and said hand mount comprising a hand grip within an enclosure.

* * * * *